United States Patent
Deacon et al.

(10) Patent No.: US 11,590,058 B2
(45) Date of Patent: *Feb. 28, 2023

(54) SYSTEMS AND METHODS FOR TREATMENT ADHERENCE IN SUBSTANCE ABUSE TREATMENT

(71) Applicant: Ria Technology Management Inc., San Francisco, CA (US)

(72) Inventors: David A. G. Deacon, San Francisco, CA (US); Robert P. Nix, San Francisco, CA (US); John E. Mendelson, San Francisco, CA (US)

(73) Assignee: Ria Technology Management Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/646,595

(22) Filed: Dec. 30, 2021

(65) Prior Publication Data
US 2022/0117851 A1 Apr. 21, 2022

Related U.S. Application Data

(63) Continuation of application No. 17/099,282, filed on Nov. 16, 2020, now Pat. No. 11,234,902, which is a continuation of application No. 16/813,398, filed on Mar. 9, 2020, now Pat. No. 10,864,143, which is a continuation of application No. 15/851,246, filed on Dec. 21, 2017, now Pat. No. 10,617,606.

(60) Provisional application No. 62/438,083, filed on Dec. 22, 2016.

(51) Int. Cl.
| | | |
|---|---|---|
| A61J 7/04 | (2006.01) | |
| G16H 20/10 | (2018.01) | |
| G16H 40/67 | (2018.01) | |
| A61J 1/03 | (2023.01) | |
| A61K 9/20 | (2006.01) | |
| G16H 10/60 | (2018.01) | |

(52) U.S. Cl.
CPC ............ *A61J 7/0409* (2013.01); *G16H 20/10* (2018.01); *G16H 40/67* (2018.01); *A61J 1/03* (2013.01); *A61J 2200/30* (2013.01); *A61K 9/20* (2013.01); *G16H 10/60* (2018.01)

(58) Field of Classification Search
CPC ........ A61J 7/0409; A61J 1/03; A61J 2200/30; G16H 20/10; G16H 40/67; G16H 10/60; A61K 9/20
See application file for complete search history.

(56) References Cited

U.S. PATENT DOCUMENTS

| | | | | |
|---|---|---|---|---|
| 5,852,408 | A | * 12/1998 | Christiansen ......... | A61J 7/0436 340/568.1 |
| 7,641,611 | B2 | 1/2010 | Hawthorne et al. | |
| 8,701,815 | B2 | 4/2014 | Polzius et al. | |

(Continued)

*Primary Examiner* — James J Yang
(74) *Attorney, Agent, or Firm* — Nixon Peabody LLP

(57) ABSTRACT

Patients with substance abuse problems may be prescribed regular medication that dulls the positive effects of the substance. However, one of the largest challenges for substance abuse patients is that many do not regularly take their medication as they want to experience the high of the substance. Accordingly, systems and methods have been developed for medication sessions that distract the patient from taking the medicine by incorporating the reminder and other med actions in close temporal proximity.

14 Claims, 6 Drawing Sheets

(56) References Cited

U.S. PATENT DOCUMENTS

| | | |
|---|---|---|
| 8,707,758 B2 | 4/2014 | Keays |
| 2013/0168175 A1 | 7/2013 | Polzius et al. |
| 2013/0216989 A1 | 8/2013 | Cuthbert |
| 2014/0210627 A1* | 7/2014 | Nothacker ............ A61B 5/4845 340/576 |
| 2015/0111187 A1 | 4/2015 | Loeb et al. |
| 2015/0137972 A1 | 5/2015 | Nepo |
| 2015/0288797 A1 | 10/2015 | Vincent |
| 2016/0161468 A1 | 6/2016 | Keays et al. |
| 2016/0239635 A1* | 8/2016 | Fateh .................. A61M 15/008 |
| 2017/0283151 A1* | 10/2017 | Stormer ................. G16H 20/10 |
| 2017/0287353 A1 | 10/2017 | Kazemi et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0177684 A1 | 6/2018 | Deacon et al. |
| 2018/0182258 A1 | 6/2018 | Deacon et al. |
| 2018/0182497 A1 | 6/2018 | Deacon et al. |
| 2018/0313818 A1 | 11/2018 | Keays et al. |
| 2019/0252071 A1 | 8/2019 | Davis et al. |
| 2020/0206086 A1 | 7/2020 | Deacon et al. |
| 2021/0069066 A1 | 3/2021 | Deacon et al. |

* cited by examiner

SYSTEMS AND METHODS FOR TREATMENT ADHERENCE IN SUBSTANCE ABUSE TREATMENT

CROSS REFERENCE TO RELATED APPLICATIONS

This application is a continuation of U.S. application Ser. No. 17/099,282, filed Nov. 16, 2020, and issued as U.S. Pat. No. 11,234,902 on Feb. 1, 2022, which is a continuation of U.S. application Ser. No. 16/813,398, filed on Mar. 9, 2020, and issued as U.S. Pat. No. 10,864,143 on Dec. 15, 2020, which is a continuation of U.S. application Ser. No. 15/851,246, filed on Dec. 21, 2017, and issued as U.S. Pat. No. 10,617,606 on Apr. 14, 2020, which claims priority to and the benefit of U.S. Provisional Application No. 62/438,083, filed Dec. 22, 2016, each of which is hereby incorporated by reference herein in its entirety.

FIELD

The present invention is directed to systems and methods for treatment of substance abuse including drug and alcohol disorders.

BACKGROUND

The following description includes information that may be useful in understanding the present invention. It is not an admission that any of the information provided herein is prior art or relevant to the presently claimed invention, or that any publication specifically or implicitly referenced is prior art.

Treatment of alcohol abuse disorder and other drug addictions is done today at rehab centers where a patient is locked into a substance-free facility for a month or more. Other services may be provided by the rehab center, such as a 12-step program, education sessions, or talk therapy. These patients are stabilized by ensuring the addictive substance is unavailable for the duration of the program.

Addiction is characterized by the formation of trigger circuits in the brain which induce a craving for the addictive substance in the addict whenever the trigger behavior recurs. These trigger circuits are learned responses to otherwise-innocuous behaviors which the addict has frequently engaged in while using the addictive substance. An example of a trigger behavior for a smoker might be the completion of a meal, after which he habitually goes out for a smoke. The addictive substance (in this case nicotine) activates motivational neurotransmitters in the brain every time the substance is used, thereby building a memory pathway around the trigger behavior (completion of the meal). When the trigger behavior recurs, the trigger pathway floods the brain with motivational neurotransmitters that cause a craving for the addictive substance.

When the addict leaves rehab, his behavior triggers provide the principal challenge. The drug-free stay in the locked rehab environment will certainly have improved an addict's health, but it provides little help against those powerful urges for drug use that await in the home environment.

SUMMARY

A far better approach to treating addiction is to treat the addict in the home environment, where the behavioral triggers are present during the treatment program. Provided that the drug use can reliably be reduced or eliminated in the home environment, the addict can begin to live out different scenarios for the trigger behaviors associated with his addiction. This type of treatment program can use the neurophysiology of addiction in reverse, to begin to undo the addiction itself. New examples of the trigger behaviors that occur without drug use progressively weaken the addictive association. Maintaining such a home treatment program for an extended period of time can help addicts make real progress in regaining control of their addiction.

Of course, the simple locked-door policy of the rehab world will not work in the home environment, so a more effective treatment methodology needs to be used. In the case of addictions for alcohol and opiates, medicines are available that reduce drug use dramatically. For those addicts with a motivation to stop, these medications often allow a complete cessation of drug use while under medication. If these drugs are taken regularly, a home treatment program can accomplish significant progress for many patients, not just by reducing drug use for a period of time, but also by relearning new behaviors that create a more healthy lifestyle that can be maintained over the long term.

One of the keys to achieving this outcome is maintaining regular medication use during a treatment program where the patient is still being exposed to the full load of temptations built into his addictive lifestyle. There is a need for an adherence method of ensuring that medications are taken in the home environment despite the presence of temptations to cheat.

Many adherence methods have been tried, with spotty success. The biggest problem seems to be that if the patient, challenged by the difficulties of changing his habits, lacks powerful motivations supporting the addiction treatment, he will find ways to subvert the intervention. Excuses, in this case temporary narratives that support noncompliance with a treatment program, can be powerful barriers to a patients' success. These narratives act by enhancing attention to negative behaviors including not taking daily medications, and avoiding personal interactions with supporters who encourage behavior change.

Medical personnel are often frustrated by patients who could benefit from taking their medication, yet who nonetheless persist in skipping their doses. There is a substantial literature that has developed on the subject of adherence. Reasons for non-adherence cover a huge range from simple neglect, as in an aged person not paying enough attention or becoming confused about medications have already been taken or what day of the week it is today, to active resistance, as in patients who refuse medicines based on ideas of persecution.

Methods for overcoming non-adherence to medication instructions range from rational persuasion (it's good for you) to gamification (it's fun) and rewards (it's profitable). Our insight is that these approaches suffer from the common difficulty that they tend to emphasize the act of taking the medications. If the patient can develop an excuse that subverts the persuasion, however temporarily, the very efforts at achieving adherence instead accomplish the opposite. The disclosed technology is based upon the opposite approach: de-emphasize the medicine and find a way to distract the attention of the patient on another "shinier" object, while creating the conditions that will naturally lead to taking the medicine.

The disclosed technology was developed in the difficult field of addiction medicine, where it is notoriously hard to obtain co-operation of patients in taking their medicines because those medicines typically reduce the pleasure derived from taking the drugs the patients are addicted to.

Nevertheless, we have observed good success with patients using our novel adherence methodology.

The disclosed systems and methods provide medication reminders in the context of situations where the patient's attention is drawn by a different objective, whose purpose is different from that of the medications. Because of the distraction coming from a different direction, the patient complies with the reminder while accomplishing the other objective. For example, in the case of alcohol addiction, the patient may be prescribed a daily dose of 50 mg of the inexpensive drug Naltrexone.

This drug is FDA approved for use in alcohol addiction, is safe, and has few side effects. Yet it diminishes the patients' pleasure from binging on alcohol so there is definitely a compliance issue which interferes with adherence. We are finding good adherence results with a mobile app that reminds patients to take their medicine while occupying them with a different task: measuring their blood alcohol content with a personal wireless breathalyzer.

The breathalyzer itself plays an objective role in the patients' care plan: it measures their blood alcohol content, revealing how much they drank today, and providing a check on the self-reported number of drinks for the day. The task of using the breathalyzer commands significant attention, even though the app makes its use easy for all, and the tasks of answering the accompanying questions raise issues of reporting accuracy that are not related to the effect of the medication. The associated task of reviewing the trend of objective data over the past few weeks also remind patients of the longer term issues of behavior past and future, and reporting progress to the medical staff, that distract from the impulsive near term reward orientation associated with addiction.

This presents the ideal context in which to present one additional request: take your medicine. The "take your medicine" request preferably has a verification task associated with it, so it cannot easily be ignored. In our case, the verification task is automatically presented by the app, which takes a photograph of the pill in the patients' hand, preparing the medicine for being taken immediately by mouth. The medicine reminder is performed during the daily ritual of using the breathalyzer, which enhances adherence by de-emphasizing the medication reminder compared to the temporally adjacent task (before or after) of using the breathalyzer.

The disclosed technology prompts patients to use the app and breathalyzer once or twice a day depending on the severity of their addiction pattern. Using the breathalyzer is a multistep process, involving turning on the device and perhaps charging it, pairing with Bluetooth, warming up, blowing, reading the result, and reading a dynamic message for the patient and sometimes reviewing past progress. The breathalyzer use actually provides useful information to the addict that he can act on independently.

The app keeps track of the results, and provides a useful graphical display of progress. In comparison, the single step medicine reminder (take the photo now) becomes submerged in the attention paid to the breathalyzer process. After a week or two of usage, the breathalyzer usage becomes a multistep ritual that can be performed largely without thought. The medication reminder becomes a small piece of a different activity that is considered useful to the patient. As a result, little attention is paid to the medication reminder, and positive compliance is "borrowed" from the adjacent task of using the high-tech breathalyzer.

In a further aspect of the invention, the process of taking the photograph of the pill in the patient's hand further increases adherence and reduces the opportunity to cheat the system. In order to take the photograph, the patient must find his pills, open the bottle, and shake out a pill into his hand. At this point, the patient has completed three out of the four steps of taking the medicine. After taking the photo the quickest and easiest action available is to complete the action by swallowing the medicine. No medicine adherence tool is foolproof; this approach is both convenient and natural, which makes it effective.

In a further aspect of the invention, we provide systems and methods for empowering a spouse or significant supporter in a behavioral modification treatment program. When harmful behaviors have been learned by a patient, as is usually the case in substance abuse disorder, eating disorder, and other situations such as diabetes, the party whose life is most impacted is often not the patient, but a spouse or other person with a significant relationship with the patient. While the patient tolerates and sometimes even promotes his own harmful behavior, the spouse sees his relationship with the patient slowly eroded and suffers real anguish. Anyone who has attended both Alcoholics Anonymous meetings (for addicts) and Al Anon meetings (for family members of addicts) knows that the family members carry most of the the stress and pain caused by the addiction. These family members and close friends need support as much or more than the patient being treated.

An invention we provide is a stress reduction tool that empowers those in a patient's inner circle. Addiction is characterized by learned behaviors that an addict associates powerfully with his substance abuse actions. At and after the ball game, for example, the learned action may be for the patient and his drinking buddies to drink too much and get into fights. This behavior is completely predictable for the patient's spouse, who is far too familiar with the subsequent effects of intoxication. We provide the spouse with a tool to monitor and report back data on the intoxication condition of the patient. The spouse can then take action based upon the data, and the patient can learn to modify his behavior based upon the requirements of the spouse.

In the case of alcohol abuse, the patient uses a personal wireless breathalyzer with a DxRxMedical app to measure his blood alcohol content. The patient may use the app to measure his blood alcohol content at any time, but a spouse may be remote from the patient and unable to request a breathalyzer measurement. We provide an app for the spouse to use for this purpose. The spouse's app maintains confidentiality and limited access with a spouse login procedure. When authorized by the patient, the spouse's app provides a control functionality that allows the spouse to set up a breathalyzer action on the patient's app. The requested action may be immediate or it may be scheduled for a specific time in the future, such as at a time the ballgame is expected to end.

At the scheduled time, the patient receives an alert through the app, which may be a tone or a buzz and a screen instruction to use the breathalyzer. The breathalyzer measurement result is then communicated back to the spouse's app and the spouse is alerted to check the result when it is available. The real-time scheduling, communications, and alerting are made possible by the connectivity of the apps through the "cloud" as provided by the DxRx service. Additionally, the patient app may be configured to display dynamic messages from the spouse. The spouse may set up a message such as "Reminder: you agreed to skip the bar and come straight home." that displays if the measured blood alcohol content exceeds a threshold set by the spouse such as 0.02 for example. A different message may be set to display if the blood alcohol content is less than or equal to 0.03 such as "Way to go, John! You did it!"

As a further feature of the breathalyzer measurement requested by an inner circle member, the front facing camera of the mobile device may be activated, with the prior permission of the patient, and a photograph of the patient will be taken at the moment of sampling the patient's breath for the breathalyzer measurement. The purpose of the photograph is to ensure that the breathalyzer data are acquired for the patient and not some third party. The photograph is displayed to the patient on the patient's mobile device so that the patient is aware that the photo has been taken, and the system sends a data record to the server including the photo data. The photo is also sent to the requesting party to assure them that the patient used the breathalyzer and not some third party.

In a further aspect of the invention, we provide systems and methods for engaging an inner circle of supporters in the treatment and recovery of the patient. It is well known that social interactions with close supporters provide strong motivation. One of the consequences of addictive substances including alcohol and drugs is that addicts tend to abandon their social interactions in favor of obtaining and using the addictive substance. Rebuilding social connections is one of the most important elements in a recovery treatment program.

We have invented effective methods for establishing or renewing social connections, and for promoting frequent interactions with these connections. We provide an app functionality for the patient that allows him to work with supporters he chooses. The patient is encouraged to enroll several supporters in the program to help him with his recovery. A control function is provided in the app that allows him to send an email inviting his chosen supporters to download their own app. The control function also allows the patient to set permissions for his supporters to execute certain functions such as providing weekly behavior ratings of the patient, and receiving information about the blood alcohol measurements of the patient.

Supporters use the supporter app to receive a weekly alert with a request for a simple rating of the patient's behavior such as better/same/worse, or great/fine/neutral/poor/terrible. The rating is accomplished easily and in a short time by tapping one of the action buttons on the page, and it may be accompanied by one or two additional questions. This information is stored in a server connected to the supporter app and it is also sent to the patient so the patient is reminded that the supporter still cares about his progress. The rating process may be accompanied by an easy messaging facility between the patient app and the supporter app, allowing the supporter to suggest and arrange a face-to-face meeting, for example. This process reinforces the connection with the supporter on at least a weekly basis.

Since supporters can also see the breathalyzer measurements for the patient over time, they are in a position to communicate encouragement to the patient, reminding the patient of the progress being made, and again reminding the patient that the supporter cares about his progress. These social connections build in the patient's mind over time, ultimately giving him the motivation to undertake behavior changes considered difficult such as meeting with a therapist for example.

The system also calculates baseline levels of behavior and behavior trends from the rating data provided by the patient's supporters. Significant deviations from the current trend may be communicated to the patient's inner circle of supporters and family members, as allowed by the patient through his control function. Some deviations are negative, such as a relapse into substance abuse, and the resultant alerts may enable inner circle members to marshal additional support for the patient. Other deviations are positive, such as the first meeting with the therapist, and the alerts provided to the inner circle become reminders to provide positive feedback.

Disclosed are various systems and methods that implement these solutions. For instance, a software solution operates on the server. A version of the software is implemented as an iOS or other operating environment app that runs on smartphones. Another version of the software solution is implemented to run on browsers on some of the smartphones and on desktop or laptop computers.

A patient who is registered in the software solution may access the treatment solution through his internet connected device which may be any form of internet connected device such as a smartphone, laptop, desktop, tablet, or wearable. A medical team may serve the patient. The medical team may consist of a variety of specialties including physician, midlevel, therapist, coach, and/or counselor. After an onboarding visit between the physician and the patient, in which the patient is accepted into the physician's practice and a doctor-patient relationship is established, further communications may proceed in part through the treatment solution.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

Figure 1:
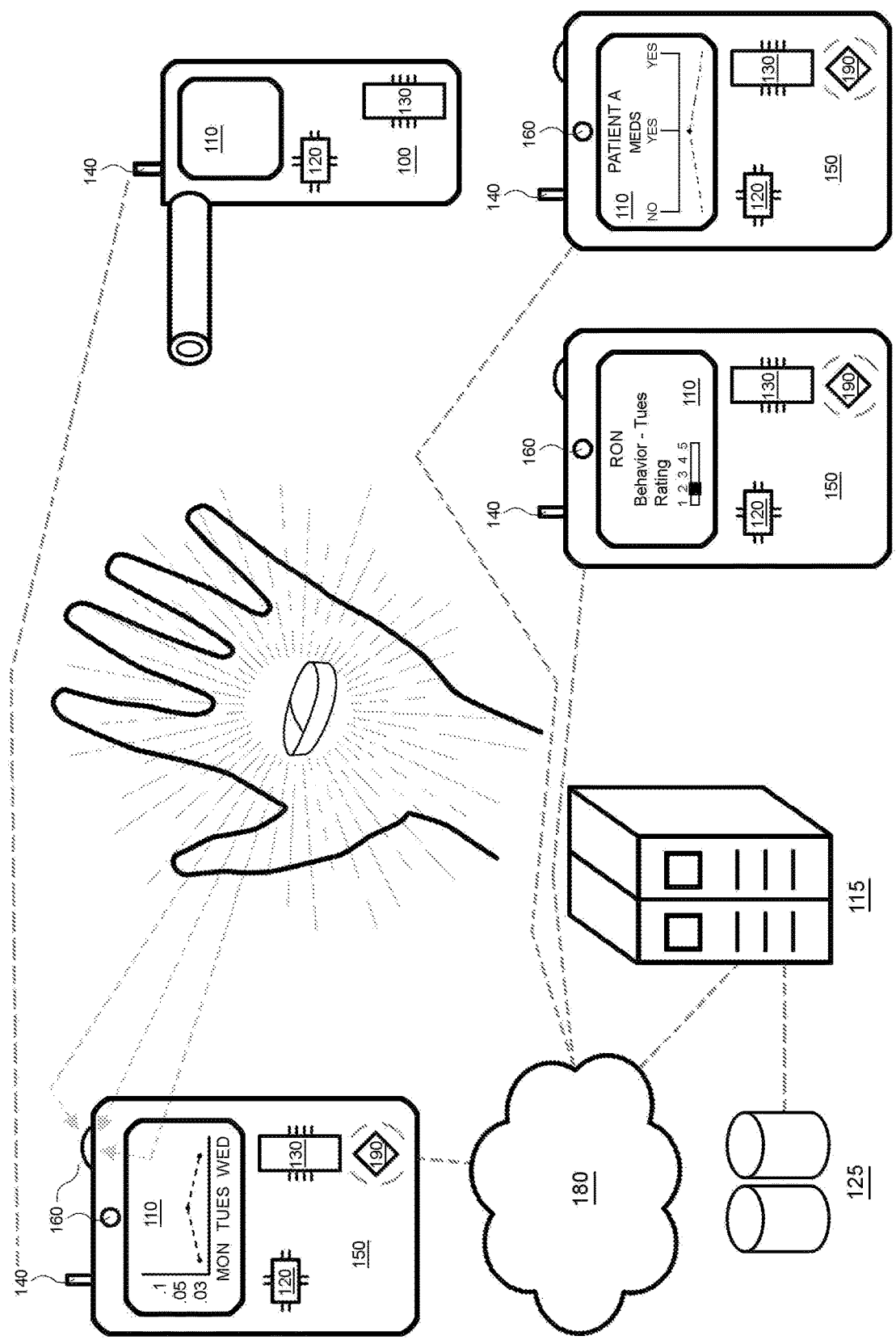
FIG. 1 depicts an example of a perspective view of a substance abuse treatment adherence system.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Overview

Disclosed are systems and methods for increasing patient compliance with a treatment adherence program. Patients with substance abuse problems may be prescribed regular medication that dulls the positive effects of the substance. However, one of the largest challenges for substance abuse patients is that many do not regularly take their medication as they want to experience the high of the substance. Accordingly, systems and methods have been developed for medication sessions that distract the patient from taking the medicine by incorporating the reminder and other med actions in close temporal proximity.

For instance, in some examples, the system includes a measurement device and a mobile device. In some examples, the system is set up for a care plan session that includes use of the hardware measurement device and a prompt to take medication in a close temporal proximity to using the measurement device. The patient's engagement with the measurement device distracts the patient from taking the medication. Accordingly, after the patient is on a regular schedule, the patient forms a habit of using the measurement device and the medication. Experimental results of the application have shown that the system can increase adherence to taking medication in alcoholics that have a treatment plan to decrease abuse of alcohol.

For instance, the mobile device may initiate the measurement device, and instruct the patient to use it. Then, the patient may use the measurement device (e.g. blow into a breathalyzer), which results are sent to the mobile device and display on the display. Then, the mobile device may automatically (within a certain span of time—before or after—using the measurement device) to take their meds. The system may also ask the patient to take a picture of the meds in their hand.

The system will send this data to a server, so that a doctor may review on her own mobile device, see the trend of the test results, the medication adherence, and the photos of the medication. Also, the doctor may update or form a new care plan that can be sent to the server on their mobile device.

Additionally, the system may link an inner circle of supporters and family members, which can rate the patient's behavior, and schedule specific breathalyzer sessions. The system may also provide a function of granting permissions enabling the patient to add individuals of his choice to his inner circle and grant them permissions to rate behavior and schedule sessions. Also, the patient's mobile device may include a craving alert button that can immediately send an alert to the doctor, the family devices or to both.

In some examples, the server may calculate thresholds (or receive them from the doctor) that send out alerts to the doctors and/or inner circle members automatically. For instance, after a measurement on a certain day, if the blood alcohol content is above a threshold the system can be set to send out an alert. Additionally, the server may record behavior ratings and determine a trend or threshold of the subject ratings. Then, the system can send a message or notification to family or the doctor if the behavior rating is outside of the trend significantly, or outside the threshold.

System Connectivity

FIG. 1 illustrates an example system that includes mobile devices 150, for the doctor, patient, and inner circle that are connected over a network 180 to a server 115 and database 125. Additionally, a measurement device 100 is connected to the patient mobile device 150 in some examples by sending a signal (e.g. Bluetooth) between the antennas 140. In other examples, the measurement device 100 may connect to the mobile device(s) 150 over the network 180 and may for instance be routed through the server 115.

The mobile devices 150 include a display 110 (that may be used for an interface to receive data and display data to a user), a control system 120 including one or more processors, a location sensor 190 (e.g. GPS), antenna 140, and memory 130. Additionally, the measurement device 100 may include a control system 120, memory 130, and antenna 140.

In some examples, the patient mobile device 150 may include a front facing camera 160 and/or a back facing camera 160. For instance, in some examples, the system will request the patient take a picture with the medication in their hand with the back facing camera 160. In other examples, the front facing camera 160 may record the patient taking their medicine.

The doctor may have a mobile device 150 connected to the system that can review data from the patient mobile device 150 stored in the database 125. This may include a history of measurement data, photographs, and other information. The system further comprises a set of security functions to restrict access to data to the appropriate parties based on their login information and security codes.

Also, a family member (e.g. spouse) may have a mobile device 150 that is connected to the system over the network 180. In some examples, the family device 150 may be able to schedule measurements with the measurement device 100, receive alerts and perform other functions as described more fully herein. In some examples, the family member mobile device 150 may be able to download the measurement data from the database 125.

Additionally, a measurement device 100 may be included for measuring the intoxication of the patient. For instance, in some examples the measurement device 100 will be a connected breathalyzer. The breathalyzer may connect to the patient mobile device 100 through Bluetooth, WiFi, or directly by plugging into a port of the smartphone.

In other examples, the measurement device 100 may be a urine test for drugs including prescription drugs, opiates, THC, etc. In these examples, the device may be connected wirelessly in the various methods discussed to receive the results. Accordingly, in this embodiment, the care plan and other information may be used to treat an opiate addiction.

Figure 2A:
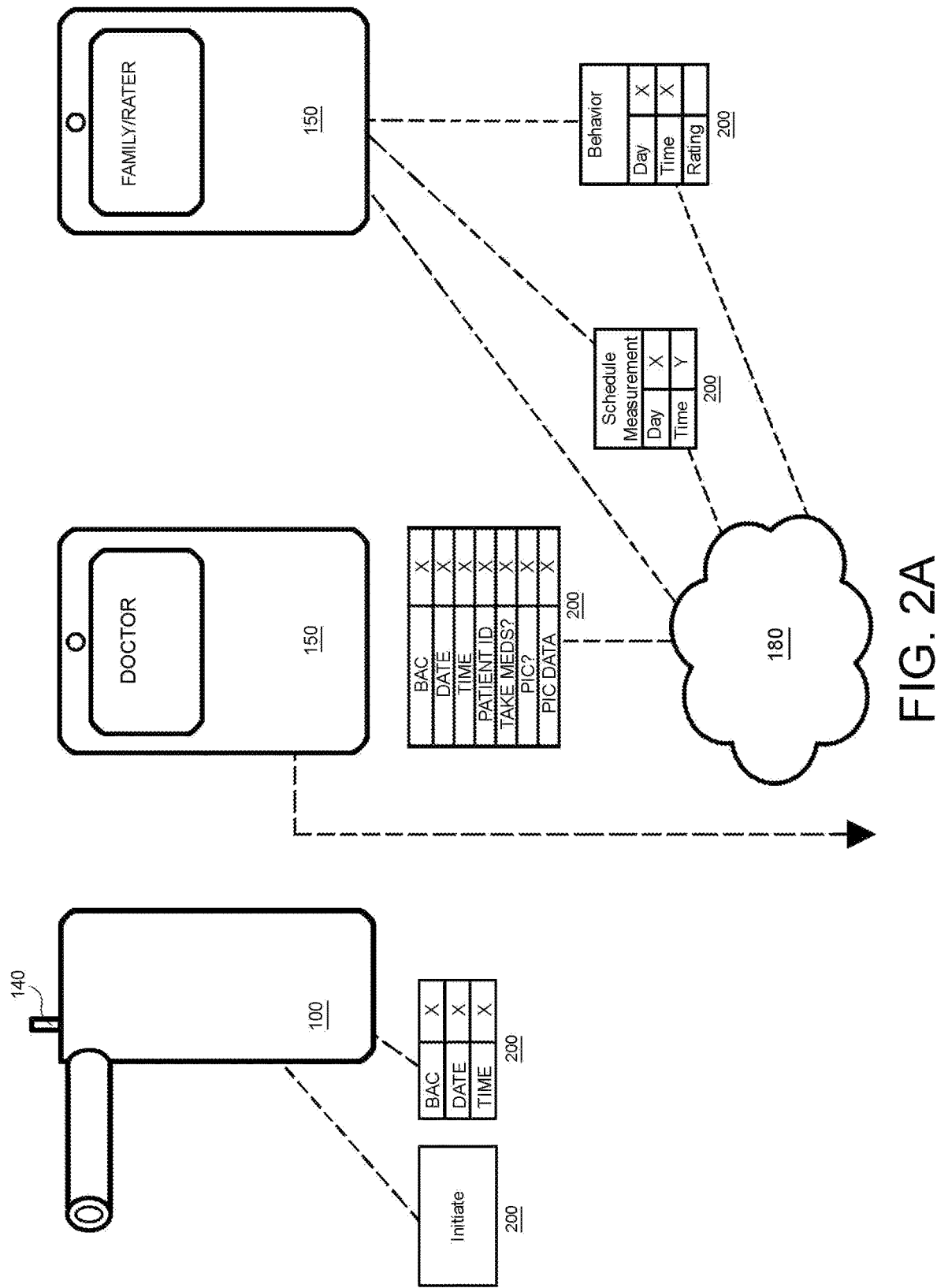
FIGS. 2A-2B depict examples of perspective views of a substance abuse treatment adherence system.
Figure 2B:
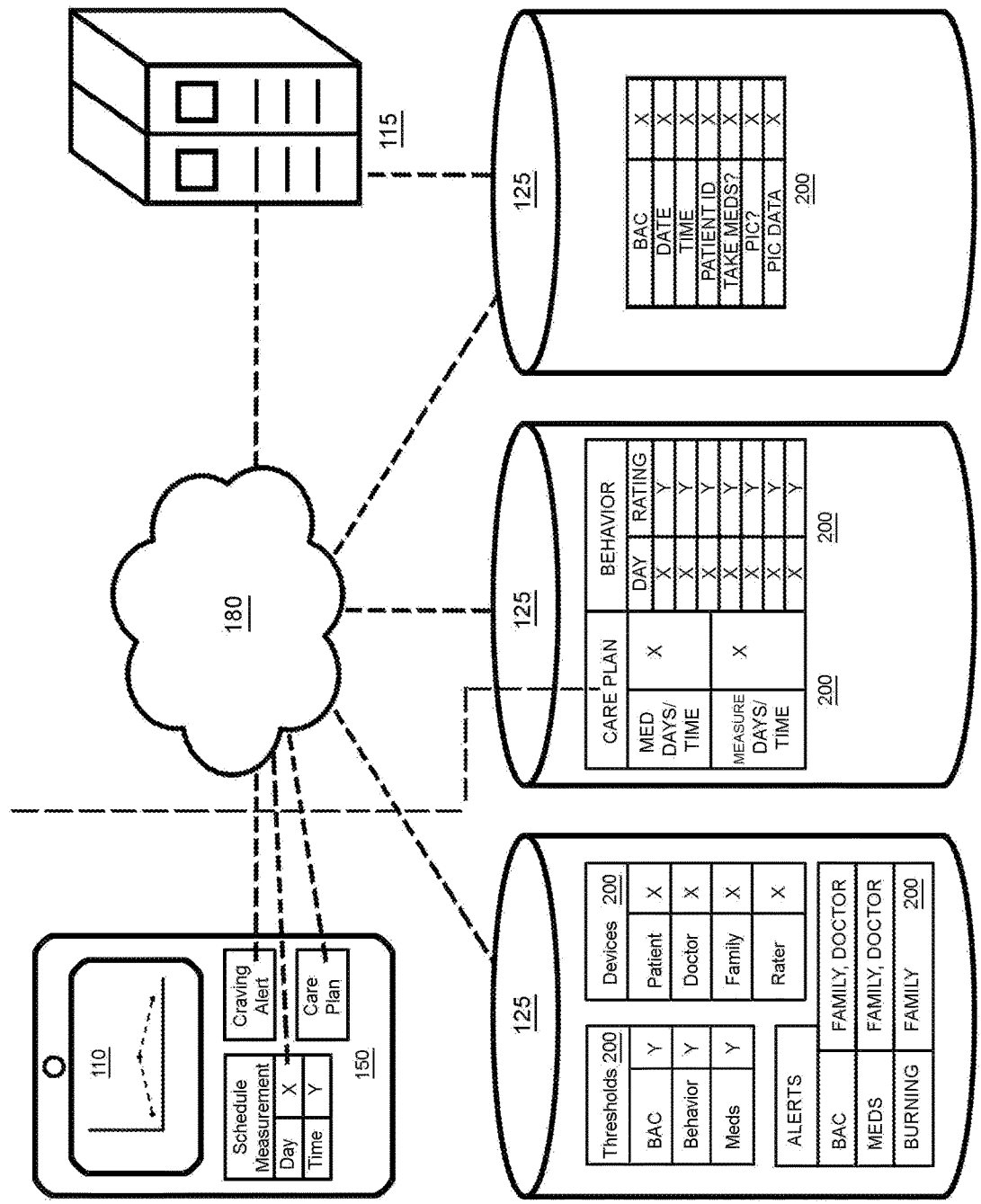

FIG. 2 illustrates an example of a system with various data structures 200 that are sent over the network 180 to the various devices of the system. For instance, the patient's mobile device 150 may first send a data structure 200 to the measurement device 100 with instructions initiate the measurement device 100 (pictured as a breathalyzer but could also be an opiate urine test, or other test for abused substances).

Then, after the measurement device captures the raw data and processes the data to output a measurement (e.g. blood alcohol content ("BAC"}), the measurement device 100 sends a data structure 200 packet to the patient mobile device 150. The data structure 200 includes one or more measurements, for instance BAC, opiate levels, or others. Additionally, the data structure 200 may include date and time stamp information.

Once the mobile device 150 receives the data structure 200, it may be stored in the mobile device memory 130. Then, then measurement data structure 200 may be sent to a server 115 over a network 180. In some examples, that data structure 200 may also include information regarding a medication session. For instance, it may include whether the patient agreed to take their medication, whether they took a picture, the data for the picture (or video), and the date and time of the picture.

Additionally, the data structure(s) 200 sent from the patient's mobile device (and most data structures sent) may include a patient identifier. The patient identifier may be a code that is referenced to the patient identifying information in a database 125. Accordingly, as the server 115 receives data from mobile devices 150 or other computing devices, the data will be stored and referenced to a specific patient in the database 125.

Each time a new measurement and medication session is initiated, the mobile device 150 and/or the server 115 and database 125 may store the session data as referenced to a session. For instance, a patient care plan may include instructions for a daily or twice daily medication and testing session. The session data 200 could then be stored referenced to the care plan expected session.

Accordingly, the session data may be accessed by the server 115 to send to the various mobile devices 150 or other computing devices connected to the network 180 for viewing or analyzing to view trends and graphs of measurements. Additionally, the system can determine which days were missed for measurements or medication based on comparing the measurement and medication data to the care plan data 200.

A doctor computing device 150 may also be connected to the system and send requests for changes to a care plan, or a request to form a new care plan. The care plan information may include the patient identifier, the medication plan which will include the medication, dosage, and the day and times for taking the medication. The doctor mobile device 150 can send a request to the server 115 to update the plan, change the dosage, frequency, or other portions of the care plan. Then, the server 115 will automatically send an update to the patient's mobile device 150 that includes the updated or changes to the care plan.

Additionally, the doctor's mobile device 150 will be able to access the measurement, and medication session data. Additionally, the doctor's mobile device 150 may be able to send messages to the patient, or schedule automatic messages to the patient after certain events. For instance, after the patient takes their meds or takes a picture, the doctor or system can schedule an automatic notification or message to the patient that congratulates them on taking the medicine that will be displayed on the display 110 of the patient' mobile device 150.

The family or friend mobile device 150 may be able to send requests to the server 115 that are forwarded to the patient's mobile device 150. This may include scheduling a request for measurement at a certain time. For instance, the family (e.g. spouse) mobile device 150 could send a data packet 200 that includes instructions to schedule or notify the patient for a measurement that is outside of the patient's care plan that may optionally include a threshold BAC or other measurement. This may be useful if the patient's spouse knows the patient will be in a trigger environment, for example a sporting event. Then, the patient may be required to take a measurement at the end of the game.

If the patient does do the measurement near when requested, and the measurement is over threshold indicated in the data structure 200 from the family members mobile device 150, the patient mobile device 150 or server 115 may send an alert to the family mobile device 150. This alert may include and indicate that it is over a threshold amount, and may optionally include the measurement reading.

The family or rater mobile device 150 may also include an interface for rating the behavior of the patient. In some examples, the server 115 may send a request to the family/rater mobile device 150 to rate the behavior of the patient, on a quantitative scale that would be a subjective rating. Then, the family member would enter the rating into the mobile device 150, which would be sent as a data structure 200 to the server 115 and stored in a database 125. The data structure 200 may include a day and time data, a rating, and other information including a patient identifier. The rating behavior may be stored in the server 115, referenced to the particular patient. To preserve patient compliance with the system, it is preferable to include patient control in the form of permissions for people to join his inner circle and provide ratings. The patient permissions can be allocated individually to family members, close friends, authority figures, and others the patient may select to join his inner circle as his supporters. Separate permissions may be allocated for different classes of activities, including for example providing periodic behavior ratings and receiving Craving Alerts.

The server 115 and database 125 may also store various permissions and automatic protocols for sending alerts in various situations. For instance, if a measurement, medication session adherence, or behavior rating is outside of a trend or threshold, the server 115 may automatically send alerts based on the protocol stored in the database 125 for that particular issue. The patient, doctor, or family mobile device 150 may be able to adjust the threshold or setting for sending automatic alerts, text messages, or other notifications.

In some examples, those device may be able to set a threshold measurement, behavioral, or other quantitative value for notifications. Also, those device may be able to set the types of notifications they would like to receive, for instance the family member may only want notifications related to measurements and not behavior. Accordingly, these preferences may be stored on a database 125 by the server 115. Therefore, when new measurements, ratings, or other data comes into the server 115 to be processed, the system can determine whether any alerts should be issued, and which devices to send the alerts.

Methods—Care Plan Session

Figure 3:
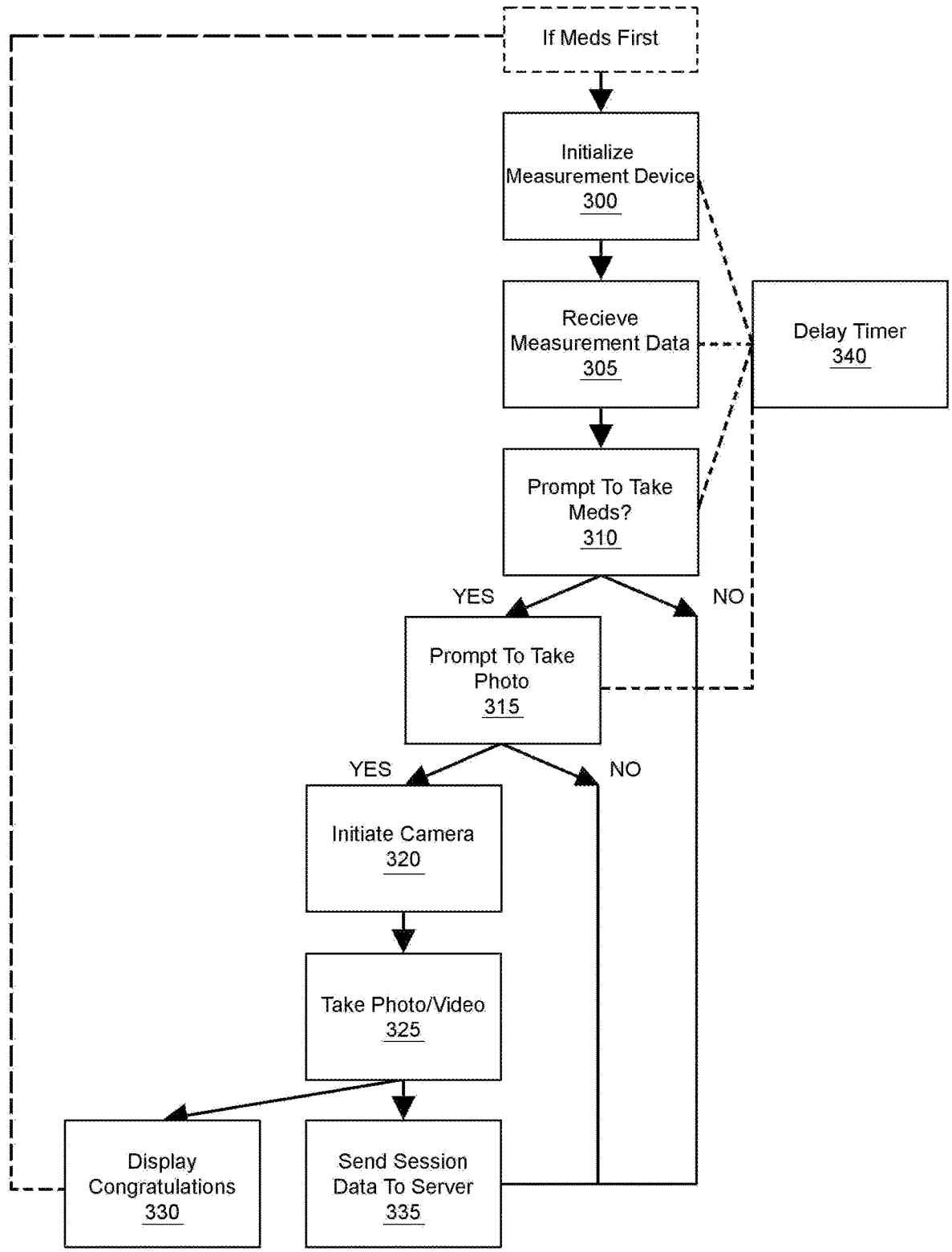
FIG. 3 depicts an example of a method for implementing a treatment adherence system.

FIG. 3 is a flow chart depicting an example method for implementing a care plan session on a smartphone and associated measurement device. In this example, the interactions on the interface of the patient's mobile phone 150 are done in close temporal proximity to the interactions to use the measurement device 100. This helps distract the patient from the medication, to increase the patient's compliance with the care plan.

For instance, first a software application running on the control system 120 of a patient's mobile device 130 may send a notification to the display 110 for a care plan session that may include either or both of a measurement and a medication taking session. Then, the user may use the interface (e.g. display, touchscreen, buttons) to accept or confirm they would like to begin a session.

If so the application may (or after the medication portion) send a data request to the measurement device 100 to initiate a measurement session 300. Initializing may include turning on, charging, pairing, warming up, blowing, analyzing or reading out with the device 100. In some examples, the application running on the patient's device 150 may display instructions to the patient on the display 110 and also send data packets 200 with instructions for each step of the measurement device's 100 measurement session. In other examples, one initiated by the application on the patient's device 150, the measurement device 100 may follow a protocol for the measurement.

After the measurement is completed, the measurement device 100 may send the measurement data so that measurement data is received 305 by the patient's mobile device 150. In other examples, the measurement device 100 may send the data to the server 115, and the server 115 may send the patient device 150 an update that the data has been received including data with the measurement.

After the measurement data has been received 305, the system will automatically display a question or other notification to the patient as to whether they will take their meds 310. In other examples, the medication question may be first when the care plan is initiated, and next after the medication portion is complete the system may automatically initiate the measurement protocol.

After the system asks the patient if the patient would like to take their meds 310, the patient may confirm or answer yes or no. If the patient answers no, then the session may terminate and the mobile device 150 may send the session data to the server 335. If the patient confirms or says yes, then the mobile device 150 may prompt the user to take a photo 315 or provide some other image data.

For instance, the device 150 may request the patient (e.g. through the display 110) take a photo of the pill in the patient's hand 315. If the patient says no, then the session data will again be sent to the server 335. If the patient says yes, then the instructions running on the control system 120 may automatically initiate the camera 320 function on the mobile device 150. This will allow the user to take a photo while still running the care plan session so the patient's session is not interrupted (which increases adherence).

In some examples, the camera will capture image (still or video) data 325 of a patient's hand 315 with a pill in the patient's hand. That way, the patient will have the pill out of the container already, and be quite close to taking the pill. In other examples, a front facing camera may take a video of the patient consuming the pill—for instance by taping a few seconds after the patient confirms through the interface the patient intends on taking the pill. In other examples, the back facing camera 160 may be used to take photos or video.

After the medication session is finished, the mobile phone 2150 may automatically display a congratulatory notification 330, or an automatic message crafted and sent from the doctor mobile device 150. Additionally, the session data will be transmitted to the server 335 by the patient's mobile device 150.

Methods—Delay Timer

In some examples, a delay timer 340 will be inserted between some of the steps in the care plan management session. The delay timer 340 may be any timer running on the application of the mobile device 150 run by the control system 120 that introduces a few seconds, 4 second, 5 second, 10 second, or any other suitable delay that is not too long between steps.

For instance, the steps of initiating the measurement device 300, pairing the Bluetooth, or other steps may introduce a few second delay. This has been found through research to help adherence by allowing a patient to reflect on their condition and its consequences during the care plan session protocol. Accordingly, the mobile phone 150 application automatically advances the care plan protocol between steps, and the delay timer 340 may put a certain delay between steps. In some examples, the doctor computing device 150 may be able to adjust the delay by patient and feedback. In other examples, the patient can turn off the feature through the interface (e.g. touchscreen) on the patient mobile device 150.

In some examples, the amount of delay may be variable. Accordingly, the delay may be from 2-5 seconds. The counter could use a base amount of 2 seconds, and then use a random number generator to add a random amount of time between 0-3 seconds to the 2 seconds to determine the total delay for a given step. The difference in delay may be important to keep the patient's attention, because the patient will not then get used to a certain delay, and will remain attentive to the device until the delay is finished.

Methods—Alerts Based on Threshold

Figure 4:
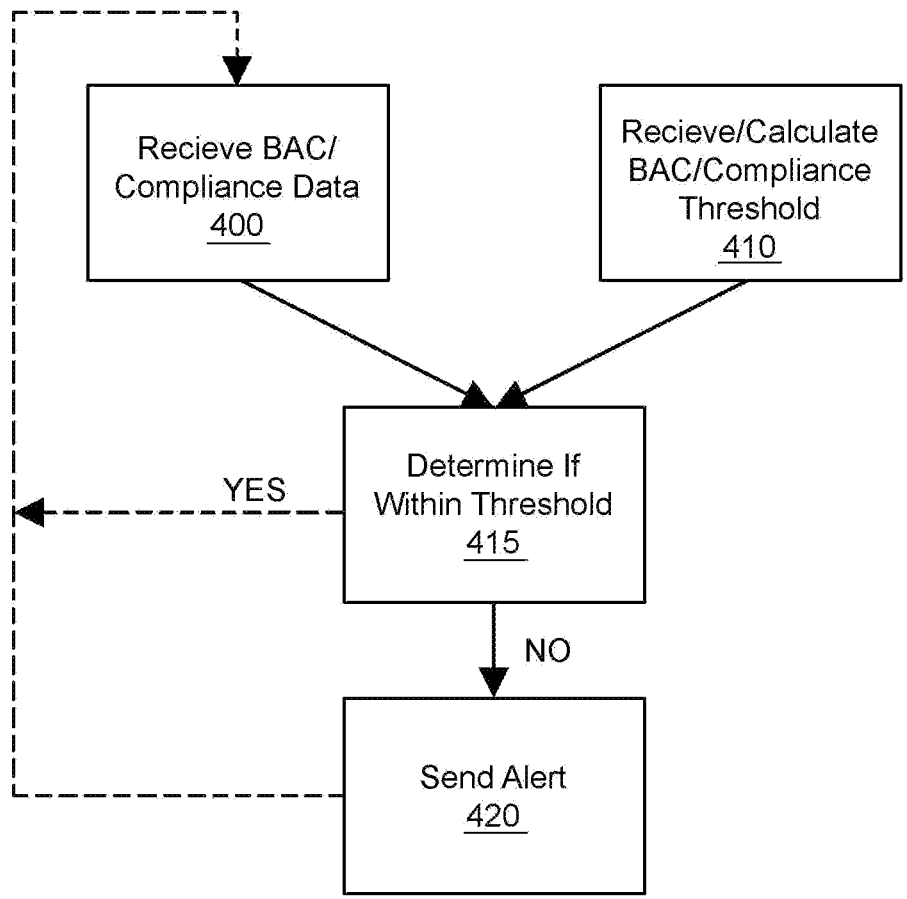
FIG. 4 depicts an example of a method for sending an alert if the system determines a measurement or compliance metric is outside of a threshold.

FIG. 4 illustrates a method the system (e.g. the server control system) may utilize to determine a threshold, and send an alert or message to various mobile devices 150 linked to the patient account if the threshold is crossed. For instance, the system may receive a measurement data or compliance data 400 that may include measurement amounts and/or information representing whether the meds or pictures were taken on particular days.

Then, the system may receive a measurement or compliance threshold 410 from the care team (e.g. doctor mobile device 150). The measurement threshold may be determined by a doctor and entered into the mobile device 150 or may be calculated based on past usage data. For instance, the server 115 may calculate a moving average of the past three weeks. In some examples, that could be for each separate weekday, as substance abuse may be greater on the weekends. In some examples, the patient or family member may enter a threshold into their mobile device 150 which could be saved and stored in the database 125, or only on the patient mobile device 150.

Then, when a new measurement is received by the server 115, or data relating to a medication session is received by the server, that data could be compared to a stored threshold to determine whether it is within the threshold 415. If it is, then the system may do nothing, and continue to receive compliance data 400 and calculate new thresholds 410 if applicable.

However, if the new compliance data 400 received is not within the threshold, then the server may send an alert 420. This alert could be messages sent to the doctor, family member, patient, and other associated mobile devices 150 (or a subset as disclosed herein). The alert may include the various information disclosed herein, including the information related to the deviation from the threshold. For instance, if the patient does not take their meds for a few days, the system could send an alert indicating that the patient has not taken their meds, and provide an option for the physician to automatically respond with a message that indicates that they should have a call.

In some examples, the system may indicate an alert 420 when the start time or compliance time follows a trend that is outside of a threshold. Research indicates that when a time for taking medication begins to deviate or get erratic, the patient is less likely to follow through on their care plan. Accordingly, the system may record an average start time for a care plan session, and determine a threshold deviation over a certain number of days when a doctor should be notified. In other examples, the threshold may be a window around the care plan set time created by the patient on their mobile device 150.

Methods—Alerts Based on Behavior Rating

Figure 5:
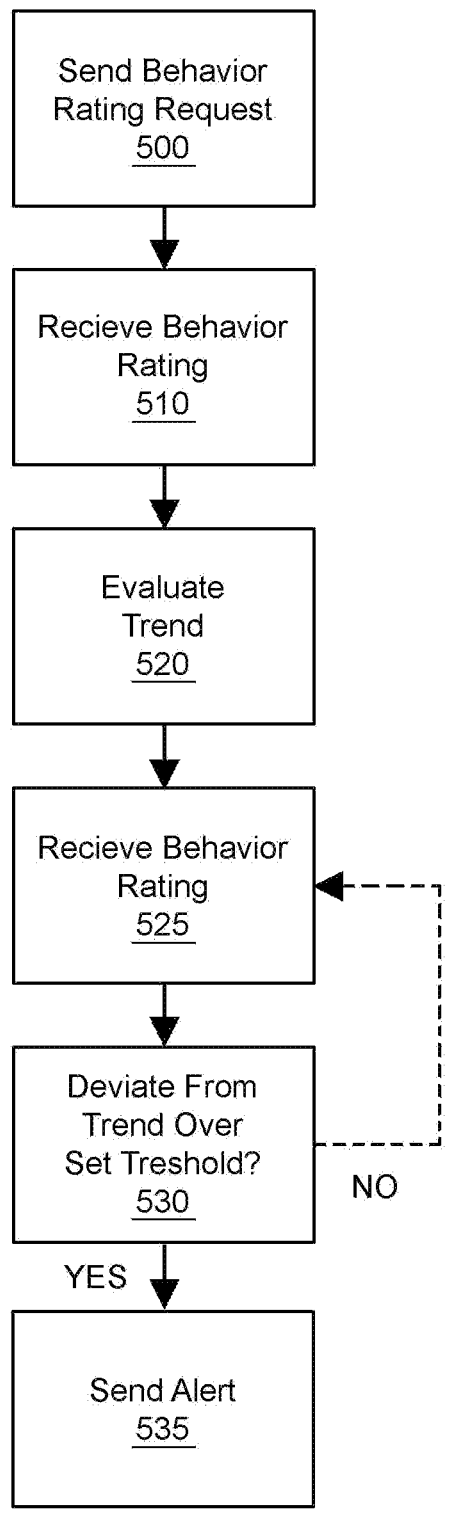
FIG. 5 depicts an example of a method for rating a behavior of a patient and sending an alert if the behavior deviates outside a threshold.

FIG. 5 illustrates an example of a method implanted by the server 115 that sends alerts if the behavior ratings fall outside of a trend—which could be positive or negative. For instance, the server 115 may send a request to a family mobile device 150 or other rater that is associated with the patient. The request may include a survey to rate the patient's behavior that week, that day or over some other time period.

In some examples, the rater's mobile device 150 may automatically request the rater to enter in a rating. Additionally, the patient may indicate which mobile devices and which accounts will rate the patient.

The rating may be a scale of 1 through 5 or other suitable scale that indicates overall the behavior of the patient. In some examples, the rating may be:
 1—Terrible
 2—Poor
 3—Neutral
 4—Doing fine
 5—Really Great The rating request could be a text message that the rater responds with 1-5 as an answer. In other examples, it could be an email, or an automated notification that opens the application on the rater's mobile phone 150. In other cases the behavior rating may be on a relative scale: "Evaluate the patient's behavior in the current period compared to the time of your last rating:
 1. Better
 2. Same
 3. Worse Then, the rater's mobile device 150 will send the rating data so it is received 510 by the server 115. The server 115 may then use the new data to evaluate the trend 520 of the behavior, by determining a baseline or an average rating for that patient for a number of prior weeks and a trend that includes the best fit rate of change. The trend calculation is constrained by the statistical properties of the data, with poor statistics, i.e. a standard deviation comparable to the rate of change times the time period of the data, yielding a flat trend with no rate of change. For some patients, they may have two or three raters, and each of their ratings may be averaged together. In other examples, the server 115 may average each rater's rating separately for a certain period of time to determine a current baseline rating.

Then, if a new behavior rating is received 525 at a future time period, the system may then compare the new rating to the trend to determine whether the new rating(s) deviate from the trend over a set threshold 530. The noise in the rating may be 0.7 points for example, and therefore, if the current rating is 3.2, the system may not send a notification or alert 535 unless the rating falls below 2.5 or exceeds 3.9. The notification is for the purpose of attracting appropriate attention to the change in the behavior rating. Additional information may in some cases accompany the notification, as in the example where immediate action is indicated based on a specific rating received. In other cases, the notification of a deviation is sufficient, as an interested party can query the system database to receive the specific rating received as well as other information.

If the behavior rating is over a threshold 530, then the server 115 may send an alert 535 to the appropriate mobile devices 150. For instance, the system may only send a notification to the doctor 150, since the raters and the family may already be aware of the behavior. In some examples, the patient will receive alerts or notifications to reinforce or give support. The message to the doctor's mobile device 150 may include a graph or table of the ratings over a set time period, and allow the doctor to decide how to proceed.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A method for implementing a treatment program adherence protocol, the method comprising:
   receiving, from a mobile device, a data structure with instructions to initiate a measurement session;
   delaying sending the data structure with instructions to initiate the measurement session to a measurement device by a preset amount of time determined using a counter running a control system;
   receiving measurement data outputted from a sensor of the measurement device;
   calculating an intoxication level based on the measurement data;
   sending a measurement data structure to the mobile device, the measurement data structure including data representing the intoxication level; and
   initiating, in close temporal proximity to the measurement session, a medication session, the medication session including:
      initiating a reminder, on a display, to ask a patient whether they took their medication today as prescribed;
      receiving, through an interface associated with the display, the patient's response to the reminder; and
      sending, to a server, a care plan session data structure that includes a date and time stamp, and information representing the patient's response to the reminder.

2. The method of claim 1, wherein the patient's response to the reminder includes one or more of the following: an input through the interface that represents a response to a question displayed on the display, an input representing a contact of the patient in a defined area of the display, a motion pattern detected by a motion sensor related to swallowing of a pill, and audio data that represents a sound related to swallowing a pill.

3. The method of claim 1, wherein the patient's response to the reminder includes audio data related to the patient speaking a confirmation they have taken a pill.

4. The method of claim 1, wherein in close temporal proximity further includes after the measurement session.

5. The method of claim 1, further comprising displaying, on the display, the intoxication level.

6. The method of claim 1, wherein in close temporal proximity further comprises before the measurement session.

7. The method of claim 1, further comprising initiating the measurement session at regular intervals.

8. The method of claim 1, further comprising initiating the medication session at regular intervals.

9. The method of claim 1, wherein the medication session further includes:
   initiating a request for patient photo input as to whether the patient is ready to take a photo of the medication;
   receiving the patient photo input and determine whether a camera function would be initiated; and
   if the camera function is initiated, taking a photograph once patient instructions are received through the interface to take a photograph.

10. The method of claim 1, further comprising in response to the medication session, sending image data representing the photograph to the server.

11. The method of claim 1, wherein the measurement device is a breathalyzer.

12. The method of claim 1, wherein the measurement device is a urine based drug test.

13. The method of claim 1, wherein the preset amount of time is between two and five seconds.

14. The method of claim 1, wherein the counter uses a fixed time of two seconds, and adds a variable amount of time each session based on a random number generator that generates a number between zero and three seconds.

\* \* \* \* \*